United States Patent [19]

Hajos et al.

[11] 4,102,929

[45] Jul. 25, 1978

[54] ASYMMETRIC SYNTHESIS OF ORGANIC COMPOUNDS

[75] Inventors: Zoltan George Hajos, Upper Montclair; David Richard Parrish, Glen Ridge, both of N.J.

[73] Assignee: Hoffmann-La Roche Inc., Nutley, N.J.

[21] Appl. No.: 723,130

[22] Filed: Sep. 14, 1976

Related U.S. Application Data

[60] Division of Ser. No. 467,356, May 6, 1974, abandoned, which is a division of Ser. No. 96,597, Dec. 9, 1970, Pat. No. 3,975,440, which is a continuation-in-part of Ser. No. 4,762, Jan. 21, 1970, abandoned.

[51] Int. Cl.$^2$ .............................................. C07C 49/76
[52] U.S. Cl. .............................................. 260/590 FA
[58] Field of Search .............................. 260/590 FA

[56] References Cited

U.S. PATENT DOCUMENTS

| 3,155,729 | 11/1964 | Johns ............................. 260/590 FA |
| 3,317,566 | 5/1967 | Stanley et al. ................. 260/590 FA |
| 3,501,530 | 3/1970 | Los ................................ 260/590 FA |

*Primary Examiner*—James O. Thomas, Jr.
*Assistant Examiner*—James H. Reamer
*Attorney, Agent, or Firm*—Samuel L. Welt; George M. Gould; Raymond R. Wittekind

[57] ABSTRACT

Optically active organic compounds are prepared starting from optically inactive reactants by means of an optically active agent which influences the course of the reaction. In particular optically active compounds having a "meso" type carbon atom undergo an intramolecular ring closure in the presence of an optically active agent to yield an optically active product having one additional ring. The present process is particularly useful in the preparation of optically active bicyclic diketones which are important intermediates in the total synthesis of steroids.

3 Claims, No Drawings

ASYMMETRIC SYNTHESIS OF ORGANIC COMPOUNDS

RELATED APPLICATIONS

This is a division of application Ser. No. 467,356, filed May 6, 1974, now abandoned, which is a division of application Ser. No. 96,597, filed Dec. 9, 1970, now U.S. Pat. No. 3,975,440, issued Aug. 17, 1976, which in turn is a continuation-in-part of Ser. No. 4,762, filed Jan. 21, 1970, now abandoned.

BACKGROUND OF THE INVENTION

One striking property of biological systems is the stereospecificity associated with many of the processes. Thus, the majority of chemical substances formed and broken down in metabolic processes are optically active and, of the two possible stereo-isomeric forms in which such substances can exist, only one is usually formed in these processes and found in natural products. In the case of the α-amino acids, e.g., only the L-members occur extensively in nature. This stereo-specificity plays an important role in the development of compounds for pharmaceutical utility. It has been found on many occasions that the physiological activity of a particular compound resides almost exclusively in one of its stereo-isomeric forms. Thus, the other stereo-isomer which may be present plays the role of an inert substance with regard to desired pharmaceutical activity, but such isomer can contribute to certain undesirable side effects. Thus, it has become of great importance to the pharmaceutical industry to provide processes for the preparation of specific optical isomers of physiologically active compounds.

The classical chemical procedure to accomplish this involves the procedure known as resolution. In this technique a racemic mixture of the compound is reacted with an optically active reagent to form a diastereomeric mixture of the substrate. These diastereomers have different physical characteristics from each other and therefore may be separated by conventional procedures such as fractional crystallization, distillation, etc. One of the diastereomers may then be converted to the desired optical isomer of the starting compound by conventional techniques such as hydrolysis. This procedure suffers from the obvious disadvantage of yielding only a theoretical maximum of 50 percent of the desired stereo-isomer based on the racemic starting material. Due to the number of reaction and purification steps involved, practical yields are substantially lower than this figure.

An alternate procedure employs reagents of biological origin such as enzymes which possess many asymmetric centers and hence are themselves highly asymmetric. In such procedure the racemic mixture is treated with an enzyme which will interact with only one of the two optical isomers of the substrate. In this manner either the undesired component is converted into a different derivative which may then be separated from the desired isomer of the initial compound, or alternatively the desired compound may interact with the enzyme to form a derivative which may be isolated by conventional purification techniques. Again such procedures suffer from the theoretical disadvantage of yielding a maximum of 50 percent of the desired optically active compound.

BRIEF DESCRIPTION OF THE INVENTION

The present invention relates to a novel process for the preparation of optically active compounds using an optically inactive substrate starting material. A critical feature of the process of the present invention is the utilization of specific optically active agents added to the reaction mixture to influence the formation of a product compound in a specific optically active form.

In a more specific aspect of this invention the substrate utilized in the present process is an optically inactive compound containing a 1,3-cyclic diketo moiety and a "meso" type carbon atom in the 2-position. A "meso" type carbon atom as the expression is used herein is one which contains four substituent groups having internal symmetry, two of which groups are identical (a) and two which are dissimilar (b and d). This may most conveniently be shown by the following representation

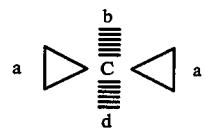

It should be noted that a plane of symmetry bisects the central carbon atom (C) and the b and d substituent groups. The resulting two halves are mirror images and cannot be superimposed. Thus, groups a, while chemically identical, are distinguishable in having a "left-handed" or "right-handed" sense associated with their orientation to the remainder of the molecule.

The cyclic substrate useful in the practice of a preferred aspect of the present invention can be represented by the following general formula:

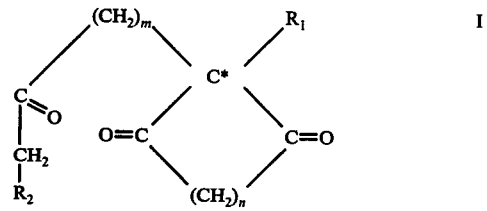

where $R_1$ is lower alkyl, aryl, aralkyl, acylamino, lower alkenyl, lower alkynyl, halogen, lower alkanoyloxy or lower alkoxy carbonyl; $R_2$ is hydrogen, lower alkyl, aryl, aralkyl and $-(CH_2)_pR_3$ where p is an integer between 0 and 2 inclusive and $R_3$ is halogen, hydroxy, lower alkoxy, mesyloxy, tosyloxy, cyano or

where $R_4$ is hydrogen, hydroxyl, lower alkyl, lower alkoxy, aryloxy, and aryl-lower alkoxy and $R_5$ is oxo, lower alkyls nedioxy or arylenedioxy provided however that when $R_4$ is other than hydrogen or lower alkyl $R_5$ is oxo; n is an integer between 1 and 5 inclusive and m is an integer between 1 and 4 inclusive.

It is to be noted in the above representation of formula I that the carbon marked with an asterisk is a "meso" type carbon. When n is an odd integer, a plane of symmetry exists in the molecule passing through the "meso" carbon and the middle methylene group of the (CH₂) portion of the ring. On the other hand, when n is an even integer the plane of symmetry bisects the central bond between two methylene groups in the same ring.

The term lower alkyl as used herein represents a straight or branched chain hydrocarbon radical having from 1 to 7, most preferably 1-4 carbon atoms. Aryl is meant to include phenyl and phenyl substituted with halogen, lower alkyl, lower alkoxy, or nitro. An example of an aralkyl group useful herein is benzyl, m-methoxybenzyl, phenethyl and m-methoxyphenethyl. Suitable acylamino groups include acetylamino and benzoylamino. The term halogen is meant to include chlorine, bromine, fluorine and iodine. Suitable lower alkanoyloxy groups include acetoxy and propionoxy for example. The term lower alkoxy carbonyl includes groups such as carbomethoxy and carboethoxy. Examples of lower alkoxy groups useful herein include methoxy, ethoxy, propoxy, butoxy and the like. Suitable alkylenedioxy groups include ethylenedioxy, 2,3-butylenedioxy and the like. Phenylenedioxy is an example of an arylenedioxy group. Lower alkenyl includes straight or branched chain hydrocarbon radicals containing a single unsaturated bond having from 2 to 7 carbon atoms such as vinyl, allyl, butenyl and the like. Lower alkynyl is intended to include groups such as ethynyl, propargyl and the like having from 2 to 5 carbon atoms.

In preferred embodiments of the present invention compounds of formula I are employed wherein $R_1$ is lower alkyl, most preferably methyl or ethyl; $R_2$ is hydrogen or lower alkyl, most preferably methyl; $n$ is 2 or 3, most preferably 2; and $m$ is 2.

It will be seen from the representation of the structure of formula I above that intramolecular nucleophilic attack by the active methylene group alpha to the carbonyl group on the side chain can occur at either of the two ring carbonyl groups. Utilization of an optically active agent in conjunction with the intramolecular ring closure conditions has been unexpectedly found to lead to a selective attack on only one of the chemically equivalent carbonyl groups thus yielding product compounds wherein one of the two possible stereoisomers will predominate.

The product formed by the above internal condensation reaction of the present invention consists of compounds of formula II or formula III or mixtures thereof, it being understood that one of the two possible stereoisomers for each compound will predominate. The relative proportion of each compound found as product will depend on the reaction conditions, e.g. solvent employed for the reaction in a manner to be discussed later.

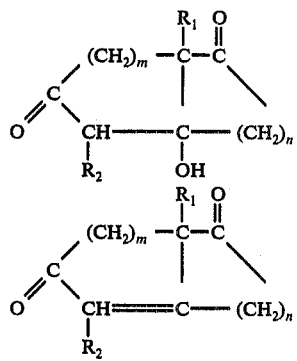

where $R_1$, $R_2$, $m$ and $n$ are as above.

The bicyclic compounds of formula III, particularly where $n$ is 2 or 3 and $m$ is 2, are useful intermediates in the preparation of steroids having known valuable pharmacological properties. These bicyclic compounds may be converted into the aforesaid steroids by procedures which are well known in the art.

The optically active agent useful in the practice of the present invention is selected from the group consisting of optically active organic compounds containing an acidic and/or basic function and more complex systems, e.g., enzymes.

Suitable optically active organic compounds containing acidic functions useful in the practice of the present invention include for example, sulfonic acid derivatives, such as (+) or (−)-10-camphorsulfonic acid.

Examples of optically active organic compounds having a basic function useful as optically active agents herein include the optically active primary and secondary amines. Suitable amines include, for example, the following: α-methyl benzylamine, lower alkyl esters of proline and the like.

Due to the fact that organic bases, like inorganic bases, can catalyze the formation of undesired bridge ketols via condensation of the side chain carbonyl group with a methylene group alpha to a ring carbonyl, it may be necessary to employ an acid to serve as a buffer in conjunction with the organic base. Acids useful for this purpose include organic carboxylic acids such as lower alkanoic acids, e.g., acetic acid, propionic acid, and the like. Phosphoric acid is an example of a suitable inorganic acid.

A most preferred embodiment utilizes an optically active organic compound having two functional groups, e.g., a carboxyl or hydroxyl moiety and also a primary or secondary amino group as substituents on the same molecule. Thus preferred optically active agents comprise the optically active α- or β-amino acids or α- or β-amino alcohols. Suitable optically active α-amino acids wherein the amino group is a primary amine include, for example, alanine, serine, threonine, valine, leucine, isoleucine, phenylalanine and tyrosine. Examples of suitable optically active secondary α-amino acids include proline, preferably S-(−)-proline, S-(−)-4-trans-hydroxyproline and L-azetidine-2-carboxylic acid. (−)-Ephedrine, and (S)-(−)-2-hydroxymethyl pyrrolidine represent examples of optically acitve secondary α-amino alcohols useful in the practice of the present invention.

The secondary α-amino acids represent a preferred class of optically active agents for use in the present invention. S-(−)-proline is a particularly preferred optically active agent.

Suitable enzyme systems for use as optically active agents include, for example, the aldolases.

The process of this invention may be conducted without a solvent or in the presence of either protic or (preferentially) aprotic solvents. Lower alkanols represent a preferred group of protic solvents. Examples of suitable lower alkanols include ethanol, 1-butanol, 2-propanol and 2-methyl-2-propanol. It has been found that the optical yield of product increases when the lower alkanol solvent is changed in the order primary→secondary →tertiary. Thus, 2-propanol and 2-methyl-2-propanol represent lower alkanols of preference. It has further been noted that when protic solvents are utilized as solvent for the purpose of the present invention the resulting product will consist in major part of the enone represented by compounds of formula III with only minor amounts of the ketol of formula II above.

As indicated, the process of this invention may preferentially be conducted utilizing aprotic solvents. Suitable aprotic solvents include benzene, tetrahydrofuran, acetonitrile and dimethylformamide, among others. Again it is desirable that the aprotic solvent have a substantial degree of polarity so as to produce the product in high optical yield. When aprotic solvents are used the major product formed corresponds to the ketols of formula II above with the enone of formula III being formed only as a minor product. The ketols of formula II are readily converted into the enones of formula III by utilizing dehydration procedures well known in the art; such as for example, by treating the ketol with a dehydrating agent e.g., para-toluenesulfonic acid in an inert organic solvent such as benzene at reflux.

The process for the preparation of optically active compounds of the present invention may be conveniently conducted at a temperature in the range of from about −5° to +100° C., most preferably in the range of from about 18° to 65° C. It is most desirable that an inert atmosphere be employed over the reaction mixture. Either nitrogen or one of the noble gases such as helium or argon may be utilized for this purpose. Generally, the reaction time will be within the range of from about 3 hours to 3 weeks, most preferably in the range of from about 16 hours to 6 days. It should be noted that extending the reaction time substantially beyond the indicated periods is not to be desired due to the possibility of undesired side reactions.

When secondary α-amino alcohols are utilized as the optically active agents in the present process oxazolidine intermediates have been isolated. It is most likely that enamine type of transition states are involved in the reaction mechanism. Thus, for example, when (−)-ephedrine having the following structural formula

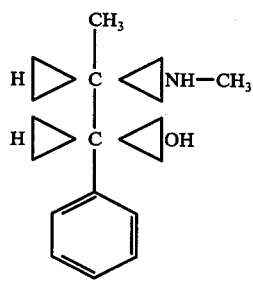

IV is utilized in conjunction with a triketone of the following formula

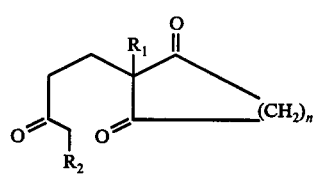

V a mixture of oxazolidine derivatives of the formula VI and VII is obtained in which one of the diastereoisomers (in this case VI) is in abundance over the other. The following mechanism was postulated for the reaction:

Reaction Mechanism

IV + V ⟶

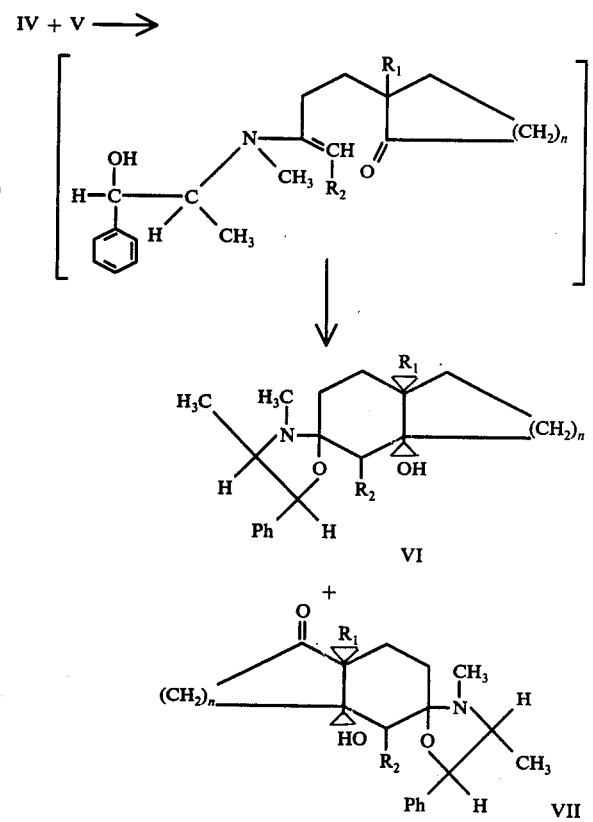

where $R_1$, $R_2$ and $n$ are as above.

The oxazolidine derivatives of formula VI and VII are readily converted to the corresponding bicyclic diketones of formula III upon hydrolysis. This hydrolysis step is conveniently achieved by utilizing aqueous acid such as, for example, aqueous mineral acid, most preferably aqueous hydrochloric acid. Conditions for such hydrolysis include a temperature in the range of from about 0° to 100° C., most preferably in the range of from about 10° to 40° C.

In a somewhat analogous fashion it is possible to postulate a transition state, when secondary α-amino acids are used as optically active agents. This involves an anchoring of the optically active reagent due to simultaneous oxazolidone ring formation and H-bonding via a protonated enamine. Thus, the following transition state is contemplated when S-(−)-proline is employed as the optically active agent for the cyclization of a triketone of formula V:

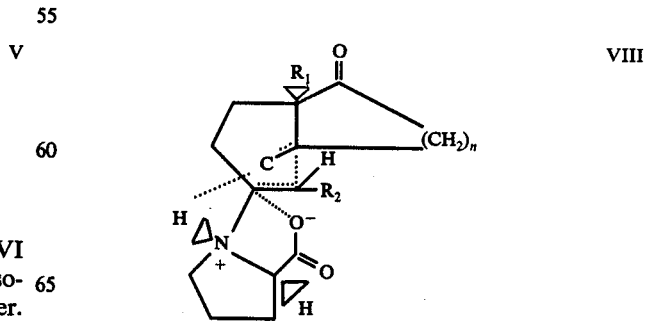

VIII where $R_1$, $R_2$ and $n$ are as above.

It should be noted in the above representation of the proposed transition state VIII for the interaction of S-(—)-proline with the triketone of formula V that the vicinal hydrogens indicated in the pyrrolidine ring of S-(—)-proline have to be on the same side of the 5-ring to allow H-bonding and oxazolidone ring formation simultaneously. This anchoring of the optically active molecule is highly important, since it provides a rather rigid transistion state in which the bulky oxazolidone ring and the angular substituent are on opposite sides of the molecule. This is then a good explanation of the high optical yield, because an involvement of the other carbonyl group of the cycloalkanedione moiety would have of lead to a sterically crowded, unfavorable transition state.

Because of excellent optical yields obtained by the use of optically active proline this compound is the optically active agent of choice in the practice of the present invention. Moreover, when S-(—)-proline is utilized with any of the ketones of formula I, the product optically active compounds obtained in major yield are found to have the requisite absolute configuration needed for intermediates in the preparation of most natural products.

It should further be noted that when the opposite enantiomer of the optically active agent is employed then the product obtained will also be the mirror image of the product obtained with the first enantiomer of the optically active agent. Thus, for example, as indicated above reaction of compounds of formula I in the presence of S-(—)-proline produces compounds of formula II and/or III which have the requisite absolute configuration found in most natural products, e.g. $R_1$ and the hydroxyl group are beta. When R-(+)-proline is employed as the optically active agent the product compounds of formulae II and/or III have the opposite configuration, e.g. $R_1$ is alpha. The latter novel compounds, particularly, those of formula II, are useful as intermediates in the preparation of terpenes having valuable fragrance properties, i.e. they may be employed as aromatic agents. The conversion of compounds of formula II to terpenes may be readily accomplished by employing the stereoselective process described by Piers et al., Chem. Comm., 1069, (1969).

A further aspect of the present invention relates to the preparation of optically active products from racemic mixtures of compounds having a true asymmetric carbon atom by the action of the optically active agents of the present invention. Thus, for example, two mole equivalents of a racemic monocyclic diketone of the following formula

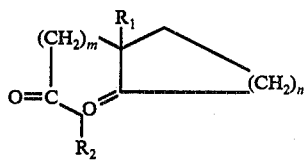

where $R_1$, $R_2$, $m$ and $n$ are as above when treated with an optically active agent, preferably an α-amino acid such as S-(—)-proline in an aprotic solvent will yield one mole equivalent of the optically active bicyclic ketol of the following formula

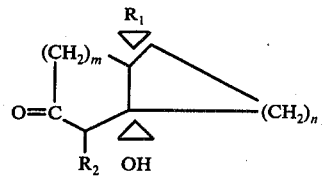

where $R_1$, $R_2$, $m$ and $n$ are as above and one mole equivalent of optically active starting material of the formula

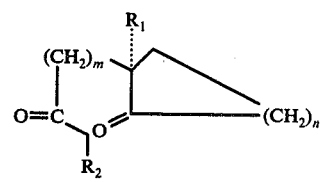

where $R_1$, $R_2$, $m$ and $n$ are as above.

It is believed that the above reaction can be explained by the fact that only one enantiomer in the racemic mixture of IX will undergo ring closure under the influence of the optically active agent while the other enantiomer will not close. The selectivity of ring closure is enhanced when a cyclic transition state similar to that shown in formula VIII is involved. Thus preferred optically active agents for this purpose include the secondary α-amino acids and α-amino alcohols. The conditions employed for this embodiment will be generally the same as described previously for the preparation of the compounds of formula II. Separation of the two optically active products X and I-a of this embodiment of the present invention can be achieved using conventional separation techniques such as fractional crystallization, chromatography and the like since the two products have different physical properties.

Compounds of formula X can be dehydrated in the manner previously disclosed to yield the corresponding enone which may then be utilized as intermediates in the preparation of 17-desoxo steroids.

A further use of this embodiment of the present invention is evident in the field of steroidal synthesis. Thus two molecules of racemic A-seco steroids of the following general formula

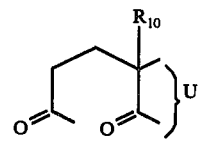

where $R_{10}$ is hydrogen or lower alkyl and U is the remainder of the B, C and D rings of the steroidal molecule are treated with the preferred optically active agents of this embodiment, most preferably S-(—)-proline in an aprotic solvent as above to yield one molecule of one specific optical isomer of the A-ring closed steroid of the formula

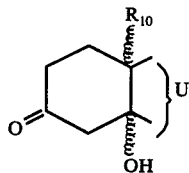

where $R_{10}$ and U are as above and one molecule of one specific optical isomer of the starting A-seco steroid compound. The nature of the optical isomers produced will depend on the specific starting material selected, the identity of the optically active agent used and the conditions employed for the reaction.

Thus it is seen from the foregoing that this embodiment of the present invention is generally useful for the preparation of polycyclic optically active ketone compounds, e.g., formula XII via aldol condensation of a racemic cyclic diketone of the general structure of compounds of formula XI. As indicated, one-half of the reaction product will be the non-ring-closed stereoisomer of the starting material now in its optically active form (XI). Products XI and XII can readily be separated by conventional techniques similar to the previously mentioned case of X and I-a.

Specific embodiments of the starting materials of formula I are novel compounds. Where $m$ is 2, these starting materials can be prepared by a novel procedure involving reaction of a vinyl ketone compound of the formula

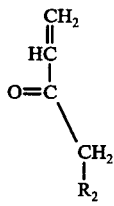

where $R_2$ is as above,
with a compound of the formula

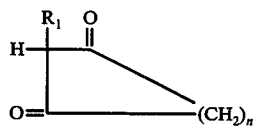

where $R_1$ and $n$ are as above. This reaction is conveniently conducted in a neutral or slightly acidic aqueous medium having a pH in the range of about 4–7, most preferably in demineralized water at a temperature in the range of from about +5° to 60° C., most preferably at about room temperature.

It is particularly important that the reaction using the vinyl ketones described above for the preparation of compounds of formula I be conducted in the absence of base. The presence of bases causes enolization of the ring ketone groups and results in the production of bridged ketols. Thus, for example, the reaction of 2-methylcyclopentane-1,3-dione with methyl-vinyl ketone in demineralized water at room temperature results in the preparation of a preferred starting material for the practice of the present invention having the following formula

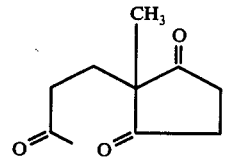

The prior art (i.e., P. Wieland and K. Miescher, Helv. Chim. Acta. 33, 2215 (1950) and C. B. C. Boyce and J. S. Whitehurst, J. Chem. Soc. 2022 (1959)) has erroneously assigned the above structure to the product of the reaction between 2-methylcyclopentane-1,3-dione and methylvinyl ketone in the presence of base. However, the compound of formula XV is an oil whose structure has been found to be consistent with observed nuclear magnetic resonance data. They reported their product as a crystalline solid which exhibited a band in the IR at 3.1μ.

However, compound XV did not exhibit a band at 3.1μ or any other band in the hydroxyl region, as expected.

The present invention is further illustrated by the following examples

EXAMPLE 1

Preparation of 2-methyl-2-(3-oxobutyl)-1,3-cyclopentanedione

A total of 65 g. of 2-methylcyclopentanedione was suspended in 136 ml. of demineralized water in a 500 ml. flask (single neck) fitted with a magnetic stirrer. To this mixture there was added at once 96 ml. of methylvinyl ketone and the system was stoppered after flushing with nitrogen. The reaction mixture was stirred at 20° C. for five days, filtered through paper on a Buchner funnel to remove a small amount of insoluble material and the resulting filtrate was shaken with 200 ml. of benzene. The resulting emulsion was treated with sodium chloride added to the aqueous portion until a good separation of phases occurred. After separation of the inorganic layer, the aqueous layer was extracted with 2 × 100 ml. of benzene and the combined organic extracts were washed with water and then with saturated saline solution. The combined organic phases were dried over sodium sulfate and then treated with stirring for one-half hour with activated charcoal and magnesium sulfate. The solids were filtered off and washed with benzene. The resulting clear dark brown filtrate was evaporated to dryness in vacuo. The charcoal and magnesium sulfate mixture was washed with 100 ml. of boiling benzene and the light brown filtrate obtained was evaporated to dryness in vacuo to give 3.84 g. of an oil which was added to the oil obtained from the main portion. A total of 100.9 g. (95.6%) yield of combined product was obtained. The entire crude oil product was fractionally distilled at 0.08–0.1 mmHg using a nitrogen capillary, pearshaped flask with a Claisen head and a water condenser. A total of 92.55 g. of product (87.6%) was obtained at a head temperature in the range of 100-109° C. as a pale yellow oil; nmr in CDCl$_3$: δ1.12 (>C—C$\underline{H}_3$), 2.22

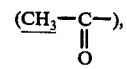

2.82 (CO-C$\underline{H}_2$-C$\underline{H}_2$-CO).

EXAMPLE 2

Asymmetric synthesis with (−)-ephedrine

A total of 1.0 g. of 2-methyl-2-(3-oxobutyl)-1,3-cyclopentanedione was dissolved in 12 ml. of benzene, 916 mg. of (−)-ephedrine was added and the resulting solution was stirred and refluxed under nitrogen for 16 hours using a Dean-Stark water separator. The reaction mixture was then treated with activated charcoal and after filtration the filtrate was evaporated in vacuo to give 1.79 g. of a gum. This gum contained a diastereoisomeric mixture of the two oxazolidines of the following structure

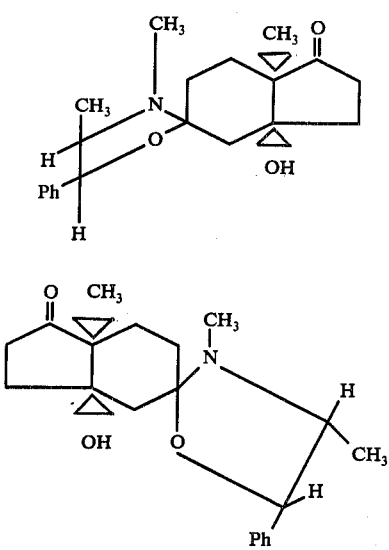

XVII

XVIII where Ph=phenyl.

The above diastereoisomeric mixture exhibited infrared absorption peaks at 3525, 1740, 1095 and 1045 cm$^{-1}$. A total of 0.9 g. of the above mixture was dissolved in 9 ml. of 1N HCl. It was allowed to stand at 20° C. for fifteen hours under nitrogen. The solution was then concentrated to a small volume in vacuo and extracted with ether. The ethereal layers were dried with sodium sulfate, filtered and evaporated in vacuo to give 340.7 mg. (75.8%) of an oil which was optically active − $[\alpha]_D^{25} = +54.80$ (c = 1.0% in benzene). This corresponded to 57.5% of the dextrorotatory bicyclic product, e.g., (+)-7,7a-dihydro-7aβ-methyl-1,5(6H)-indandione and 42.5% of the levo-rotatory bicyclic product. The product oil was found to exhibit peak maximum in the infrared spectrum at 1745 and 1665 cm$^{-1}$.

EXAMPLE 3

Asymmetric synthesis with S-(−)-proline in 2-propanol

A total of 182 mg. of the triketone 2-methyl-2-(3-oxobutyl)-1,3-cyclopentanedione was dissolved in 1.0 ml. of 2-propanol and a total of 115 mg. of S-(−)-proline was added. The mixture was stirred at 20° -22° C. for 72 hours under nitrogen. The mixture was then filtered through sintered glass and a total of 85.4 mg. of S-(−)-proline was recovered. The dark filtrate was purified by preparative thin-layer chromatography using 8 inch × 8 inch × 1 mm. thick chromatographic plates of silica gel with a 1:1 mixture of benzene-ethyl acetate as developer. The UV absorbent area gave 123 mg. (75%) of (+)-7,7a-dihydro-7aβ-methyl-1,5-(6H)-indandione. The product was found to be 82% pure by UV spectroscopy and had a rotation of $[\alpha]_D^{25} = +182°$ (c = 1.07 in chloroform). This rotation corresponds to 49.6% optical purity. The optical yield may be calculated as the ratio of optical purity to spectral purity times 100 which in the present case is found to be 60.5%.

EXAMPLE 4

Asymmetric synthesis utilizing S-(−)-proline in the absence of added solvent A mixture of 910 mg. of the triketone 2-methyl-2-(3-oxobutyl)-1,3-cyclopentanedione and 17.25 mg. of S-(−)-proline was stirred at 20° C. under argon for 12 days in the dark. The mixture was then taken up in 10 ml. of acetonitrile and filtered immediately. The filtrate was evaporated in vacuo to give 921.2 mg. of an oil. The oil was dissolved in 25 ml. of ethyl acetate and passed through 2 g. of silica gel. The silica gel was rinsed with an additional 100 ml. of ethyl acetate which was added to the first portion. The combined ethyl acetate solutions were evaporated in vacuo to give 870.6 mg. of an oil. Infrared spectroscopy and UV spectroscopy of this oil indicated that about 29.6% was (+)-7,7a-dihydro-7aβ-methyl-1,5-(6H)-indandione and the remaining major portion consisted of (+)-3a,4,7,7a-tetrahydro-3aβ-hydroxy-7aβ-methyl-1,5(6H)-indandione. The product mixture was refluxed with stirring in 15.0 ml. of 0.01 N paratoluenesulfonic acid-benzene solution under nitrogen for 15 minutes using a Dean-Stark water separator. The trap was filled with Linde type 4A molecular sieves. The mixture was cooled to room temperature and stirred with 0.3 ml. of 1N aqueous sodium bicarbonate solution for 5 minutes. It was then dried with magnesium sulfate, filtered with vacuo through paper and the solids were rinsed thoroughly with chloroform. The combined solvents were evaporated in vacuo to give 782.2 mg. of (+)-7,7a-dihydro-7aβ-methyl-1,5(6H)-indandione, $[\alpha]_D^{25} = +282.92°$ (c = 1.0 in benzene). The UV spectrum showed a maximum at 232 mu (ε = 8,870). Optical purity was calculated at 77.3% and the purity by the UV spectrum was 80.3% thereby giving an optical yield of 96.3%.

EXAMPLE 5

Acetonitrile as solvent in asymmetric synthesis

A mixture containing 1.82 g. of 2-methyl-2-(3-oxobutyl)-1,3-cyclopentanedione, 1.15 g. of S-(−)-proline and 10 ml. of acetonitrile was flushed with argon, stoppered and stirred for 6 days, preferably in the dark at a temperature of 20°-23° C. The S-(−)-proline was then filtered off on a medium sintered glass funnel and the funnel was rinsed thoroughly with acetonitrile, and then with a little ether. The total amount of S-(−)-proline recovered after drying was 1.11 g. (96.5%). The combined filtrates were evaporated in vacuo, treated once with benzene and reevaporated. The residue was dissolved in 30 ml. of ethyl acetate filtered through 4 g. of silica gel without suction and the silica gel was washed with an additional 70 ml. of ethyl acetate. The combined filtrate was evaporated in vacuo to give 1.77 g. (97.3%) of crude solid (+)-3a,4,7,7a-tetrahydro-3aβ-hydroxy-7aβ-methyl-1,5(6H)-indandione, $[\alpha]_D^{25} = +64.0°$ (c = 1 in chloroform). On examination by UV spectroscopy this crude solid was found to contain 3.7% of the corresponding dextro-rotatory enone and thus the actual rotational value of the 7-hydroxy compound should be $[\alpha]_D^{25} = +53.75°$ (89.6% optical purity). The overall yield of optically pure product was 76.37% calculated on the basis of the crude reaction product.

An optically pure sample was obtained by recrystallization from ether, and had $[\alpha]_D^{25} = +60.4°$ (c = 1.06%, in chloroform).

EXAMPLE 6

N,N-dimethylformamide as Solvent for Asymmetric Synthesis

A total of 1.82 g. of 2-methyl-2-(3-oxobutyl)-1,3-cyclopentanedione was dissolved in 10.0 ml. of anhydrous N,N-dimethylformamide (distilled from calcium hydride). To the solution a total of 34.5 mg. of S-(−)-proline was added at once. The system was flushed with argon, stoppered, and stirred magnetically at 23° C. for 20 hours. The brown-colored mixture was filtered through a medium sintered glass funnel and the filtrate evaporated with high vacuum at 22° C. (bath temperature) to give 2.4 g. of an oil. This oil was dissolved in approximately 10 ml. of ethyl acetate and filtered through 8.0 g. of silica gel. The adsorbent column was then thoroughly washed with 150 ml. of ethyl acetate, the filtrate was evaporated in vacuo to give 1.995 g. of an oil, which crystallized on seeding with authentic (+)-3a,4,7,7a-tetrahydro-3aβ-hydroxy-7aβ-methyl-1,5(6H)-indandione. The crystals were then broken up, placed under high vacuum and kept at 55° C. for 1 hour to remove the last traces of N,N-dimethylformamide. There was then obtained 1.828 g. of the aforesaid crude product in the form of a tan-colored powder, $[\alpha]_D^{25} = +56.06°$ (c = 1 in chloroform). This was equivalent to 93.4% optical purity.

A total of 1.79 g. of the above crude product was refluxed with stirring in 15.0 ml. of 0.01 N paratoluenesulfonic acid-benzene solution under nitrogen for 15 minutes using a Dean-Stark water separator. The trap was filled with Linde type 4A molecular sieves. The resulting mixture was cooled to room temperature and stirred with 0.3 ml. of 1N aqueous sodium bicarbonate solution for 5 minutes. The mixture was dried with magnesium sulfate; filtered with vacuo through paper and the solids were rinsed thoroughly with chloroform. The combined solvents were then evaporated in vacuo to give 1.6 g. (99.4%) of crude (+)-7,7a-dihydro-7aβ-methyl-1,5-(6H)-indandione as an oil which crystallized rapidly on seeding with an authentic sample; $[\alpha]_D^{25} = +321.93°$ (c = 0.935 in benzene); $\lambda_{max}^{MeOH} = 230$ mμ (ε = 10,200). This represents 87.7% optical purity and 92.4% purity by UV spectroscopy and thus it is equivalent to 94.94% optical yield. Overall yeild of product based on the trione starting material is 99.4%. Overall yield of optically pure product contained in the crude product is 87.2% by calculation based on the trione starting material.

A total of 1.564 g. of the above crude product was placed on a coarse sintered glass funnel and it was broken up in a small volume of ether. Removal of this ether by suction gave 1.107 g. of a colorless crystalline product (70.2% yield based on the trione starting material) having m.p. = 64°-65.5° C., $[\alpha]_D^{25} = +356.07°$ (c = 0.993 in benzene). This is equivalent to 97% optical purity.

EXAMPLE 7

Preparation of 2-ethyl-2-(3-oxobutyl)-1,3-cyclopentanedione

A total of 6.3 g. of 2-ethyl-cyclopentanedione was suspended in 12 ml. of demineralized water in a 50 ml. single neck flask fitted with magnetic stirrer. Then 8.3 ml. of methyl vinyl ketone was added at once and the system stoppered after flushing with nitrogen. The reaction mixture was stirred at 20° C. for 7 days, filtered through paper on a Buchner funnel to remove a small amount of insoluble material and the filtrate was then shaken with 40 ml. of benzene. The resulting emulsion was treated with solid sodium chloride to saturate the aqueous portion resulting in a separation of the phases. The organic phase was separated and the remaining aqueous layer was extracted with 2 × 20 ml. of benzene. The combined benzene extracts were washed with water and then with saturated saline solution. The organic extracts were dried over magnesium sulfate, filtered and evaporated to dryness in vacuo to give 9.91 g. of an oil. Distillation at 0.035 mmHg yielded a fraction boiling at 99-101° C. of pure 2-ethyl-2-(3-oxobutyl)-1,3-cyclopentanedione. The yield was 8.04 g.

EXAMPLE 8

Preparation of optically active (+)-7aβ-ethyl-3a,4,7,7a-tetrahydro-3aβ-hydroxy-1,5(6H)-indandione A total of 4.9 g. of 2-ethyl-2-(3-oxobutyl)-1,3-cyclopentanedione was dissolved in 25 ml. of anhydrous N,N-dimethylformamide and 0.86 g. of S-(−)-proline was added. The mixture was stirred under argon at 20°-22° C. for 20 hours. The mixture was filtered through a sintered glass funnel and the filtrate evaporated to dryness in high vacuum. The residue was dissolved in 10 ml. of ethyl acetate and it was filtered through 20 g. of silica gel. The absorbent column was washed with 450 ml. of ethyl acetate. Evaporation in vacuo of the combined ethyl acetate solutions gave 4.83 g. (98.6%) of crude (+)-7aβ-ethyl-3a,4,7,7a-tetrahydro-3aβ-hydroxy-1,5-(6H)-indandione, $[\alpha]_D^{25} = +18.09°$ (c = 1.15 in chloroform). This crude material was again passed through 20 g. of silica gel in 10 ml. of ethyl acetate as before and yielded 4.67 g. (95.4%) of a nearly colorless pasty solid. Crystallization from ether gave 3.47 g. (70.95%) of desired purified product, m.p. 111.5°-112.5° C. The product exhibited peak maxima in the infrared at 3620, 3350-3550, 1745 and 1725 cm⁻¹.

The above product may be dehydrated using the procedure of Example 6 to yield (+)-7aβ-ethyl-7,7a-dihydro-1,5-(6H)-indandione, m.p. 56°-58.5° C., $[\alpha]_D^{25} = +260.29°$ (c = 1.02 in benzene); UV max in methanol = 233-4mμ (ε = 11,570); IR max at 755 and 1680 cm⁻¹.

EXAMPLE 9

Preparation of (+)-3a,4,7,7a-tetrahydro-3aβ-hydroxy-4α,7aβ-dimethyl-1,5(6H)-indandione The procedure of Example 6 was generally followed utilizing as starting material 2-methyl-2-(3-oxopentyl)-1,3-cyclopentanedione. A total of 6 mole percent of S-(−)-proline was employed with N,N-dimethylformamide solvent at 60° C. for a total of five days. The product (+)-3a,4,7,7a-tetrahydro-3aβ-hydroxy-4α,7aβ- dimethyl-1,5(6H)-indandione was obtained as a crystalline solid m.p. 160°–161° C., $[\alpha]_D^{25}$ +34.60° (c = 1.0 in chloroform).

EXAMPLE 10

Preparation of 2-methyl-2-(3-oxopentyl)-1,3-cyclopentanedione

A total of 88 mg. of hydroquinone monomethyl ether was added to 10 ml. of ethyl vinyl ketone to stabilize the latter compound. There was then added to the above mixture 0.08 ml. of glacial acetic acid, 26 ml. of demineralized water and 11.2 g. of 2-methyl-1,3-cyclopentanedione. The resulting mixture was stirred under argon at room temperature for 15 days. An additional 9 ml. of ethyl vinyl ketone was added at the fourth day and 9.5 ml. of ethyl vinyl ketone was added at the ninth day. After 15 days, 50 ml. of benzene was added and sufficient sodium chloride was added to the aqueous phase to allow separation after shaking. The phases were separated and the aqueous phase re-extracted with 50 ml. of benzene. The combined benzene extracts were treated with a mixture of sodium sulfate, magnesium sulfate and activated charcoal. The solids were filtered off and were washed with a mixture of chloroform and ether. The combined filtrates were evaporated in vacuo and the residue was treated with an additional portion of benzene followed by concentration to dryness in vacuo. There was obtained 21.1 g. of an oil residue which was fractionally distilled at 0.05 mmHg and the fraction boiling in the range of 105°–118° C. was collected; yield 17.47 g. (89 percent). This fraction was redistilled at 0.025 mmHg to give a fraction boiling at 97°–115° C.; yield 16 g. (83.5 percent) of the above-captioned product.

EXAMPLE 11

Asymmetric synthesis using (+)-10-camphor sulfonic acid

A total of 182 mg. of the bridged ketol corresponding to 2-methyl-2-(3-oxobutyl)-1,3 cyclopentanedione was utilized in this experiment as a starting material as the bridged ketol under the conditions of the experiment was found to undergo a reverse aldol reaction to yield the aforesaid trione in solution. The starting material was treated with 60 mg. of (+)-10-camphorsulfonic acid and the mixture stirred and refluxed in 3 ml. of toluene under nitrogen using a Dean-Stark apparatus. The mixture was refluxed for 4.5 hours and then allowed to stand at 20° C. for 72 hours. The solution was washed with 0.5N sodium bicarbonate followed by washing with saturated sodium chloride solution. The organic phase was dried with sodium sulfate, charcoaled, filtered and then evaporated in vacuo to an oil which crystallized spontaneously to yield 7,7a-dihydro-7aβ-methyl-1,5-(6H)-indandione, m.p. 55°–67° C. This compound was identical to authentic material by thin layer chromatography. The product exhibited an optical rotation of $[\alpha]_D^{25}$ = +5.39° indicating an optical purity of 1.5%.

EXAMPLE 12

Asymmetric synthesis with aldolase

To 182 mg. of 2-methyl-2-(3-oxobutyl)-1,3-cyclopentanedione there was added at once 1 ml. of an ice-cold suspension of rabbit muscle aldolase in 2.0M $(NH_4)_2SO_4$ and the mixture was stirred under argon for 3 days. At this time another 1 ml. of the aldolase suspension was added and stirring was continued for an additional 5 days. The resulting solution was diluted with methanol and filtered through a sintered glass funnel. The filtrate was evaporated to dryness in vacuo and the oily residue obtained was purified by preparative thin layer chromatography to give (+)-3a,4,7,7a-tetrahydro-3aβ-hydroxy-7aβ-methyl-1,5-(6H)-indandione with an optical purity of 1.44%. This material was identified by infrared spectroscopy and by preparative thin layer chromatography with an authentic sample.

EXAMPLE 13

Asymmetric synthesis with (S)-(−)-phenylalanine

A total of 182 mg. of 2-methyl-2-(3-oxobutyl)-1,3-cyclopentanedione was dissolved in 1 ml. of 2-propanol and 165 mg. of (S)-(−)-phenylalanine was added. The mixture was stirred under argon at 20°–22° C. for 7 days. It was then filtered through a sintered glass funnel and 152.6 mg. of the amino acid was recovered. The filtrate was evaporated in vacuo to give 187.5 mg. of an oil which was purified by preparative thin layer chromatography on 20 inch × 20 inch × 1 mm thick silica gel plates; elution carried out with 1:1 benzene-ethyl acetate. (+)-3a,4,7,7a-Tetrahydro-3aβ-hydroxy-7aβ-methyl-1,5-(6H)-indandione was obtained in 36.9% yield, m.p. 107.5°–109° C. on recrystallization from ether. The product exhibited a rotation of $[\alpha]_D^{25}$ = +11.60° (c = 1.12 in chloroform) indicating an optical purity of 19.33%.

EXAMPLE 14

Asymmetric synthesis with 2S-(+)-2-hydroxymethyl pyrrolidine

A total of 182 mg. of 2-methyl-2-(3-oxobutyl)-1,3-cyclopentanedione was dissolved in 0.5 ml. of acetonitrile. To this solution there was added 101 mg. of (2S)-(+)-2-hydroxymethylpyrrolidine dissolved in 0.5 ml. of acetonitrile; the solution was stirred at +20° C. under argon. After stirring for 72 hours the acetonitrile was evaporated in vacuo and the resulting dark oil taken up in chloroform. This solution was filtered through 2 g. of silica gel, the filtrate charcoaled, filtered and then evaporated in vacuo to give 109 mg. of crude (+)-3a,4, 7,7a-tetrahydro-3aβ-hydroxy-7aβ-methyl-1,5-(6H)-indandione, m.p. 98°–102.5° C., $[\alpha]_D^{25}$ = +10.4° (c = 1.0 in chloroform) indicating an optical purity of 13.45%.

EXAMPLE 15

Asymmetric synthesis with (2S)-(−)-trans-4-hydroxy-proline

To 182 mg. of 2-methyl-2-(3-oxobutyl)-1,3-cyclopentanedione dissolved in 1 ml. of 2-propanol there was added 131 mg. of (2S)-(−)-trans-4-hydroxy-proline and the mixture was stirred under nitrogen at 20° C. for 26 days. The mixture was then filtered through a sintered glass funnel and 109 mg. of the amino acid was recovered. The filtrate was evaporated to dryness in vacuo and the oily residue obtained was purified by preparative thin-layer chromatography to give 12.1% of (+)-3a,4,7,7a-tetrahydro-3aβ-hydroxy-7aβ-methyl-1,5(6H)-indandione in 73.1% optical purity.

EXAMPLE 16

Preparation of: (−)-7,7a-dihydro-7aα-methyl-1,5(6H)-indandione.

To 182 g. of 2-methyl-2-(3-oxobutyl)-1,3-cyclopentanedione in a 50 ml round bottom flask was added 10 ml of acetonitrile. Then 1.15 g of R-(+)-proline was added all at one time, and the mixture was stirred at room temperature, in the dark and under $N_2$, for 140 hrs. The reaction mixture was cooled in an ice bath, then filtered through a sintered glass funnel, washing with 25 ml of acetonitrile (1.09 g. of R-(+)-proline was recovered). The filtrate was evaporated at 40° C, 10 ml of benzene were added and evaporated again. The resulting dark brown oil was dissolved in 15 ml of ethyl acetate and filtered through 2.0 g. of silica gel supported on a course Buchner funnel, washing with 3 × 5 ml portions of ethyl acetate. The dark brown filtrate was then filtered over 1.0 g of activated charcoal and washed with 2 × 5 ml of ethyl acetate. The filtrate was evaporated at 40° C and finally under high vacuum to yield; 1.73 g of (−)-3a,4,7,7a-tetrahydro-3aα-hydroxy-7aα-methyl-1,5(6H)-indandione as a light yellow oil; $[\alpha]_D^{25} = -57.46°$ (in $CHCL_3$, c = 1.0%). A total of 1.73g of the crude hydroxy compound was dissolved in 15 ml of benzene. This solution was placed in a 100 ml round bottom flask in a preheated oil bath (∼130°) and heated to incipient boiling when 50 mg. of p-toluenesulfonic acid was added. The mixture was refluxed with a Dean-Stark apparatus for 1.4 hours (approx. 0.2 ml. of water separated). The reaction was cooled and extracted with 15 ml of saturated sodium bicarbonate solution followed by 2 × 15 ml of saturated sodium chloride solution. The water layers were washed with 2 × 10 ml of benzene. The organic layers were collected and dried over magnesium sulfate, filtered and evaporated in vacuo. Yield: 1.2 g of a golden oil. To 1.2 g of this oil was added 6 ml of ether and 2 ml of hexane and the resulting clear solution was refrigerated overnight. The next morning the mother liquor was decanted. The crystals were washed with a cold mixture of 1 ml of ether and 0.5 ml of hexane, again decanted and the crystals finally washed with 5 ml of cold hexane. The crystals were then dried under $N_2$ at room temperature. There was obtaned 580 mg (35%) of the above titled product as white crystals; m.p. 63.2° C; $[\alpha]_D^{25} = -370.26°$ (in benzene, c=0.5%).

EXAMPLE 17

3.0 Mg. of L(−)azetidine-2-carboxylic acid was added to a stirred solution of 182 mg. of 2-methyl-2-(3-oxobutyl)-1,3-cyclopentanedione dissolved in 1.0 ml. acetonitrile. The flask was flushed with argon and stoppered and stirred at a temperature of 20°-23° C. for 6 days. The suspension was filtered and rinsed with acetonitrile and the filtrate passed through 0.4 g. silica gel without suction and the silica gel was washed with 30 ml of ethyl acetate. The filtrate was evaporated in vacuo to give 186 mg. of crude product, $[\alpha]_D^{25} +19.61°$, c=1.034% in chloroform. Thin layer chromatography showed the presence of a large amount of starting material and purification was accomplished by preparative thin layer chromatography on silica gel with 1:1 benzene-ethyl acetate to give 93 mg. (51%) of crystalline (+)-3a, 4,7,7a-tetrahydro-3aβ-hydroxy-7aβ-methyl-1,5(6H)-indandione, $[\alpha]_D^{25} +38.55°$, c=1.036% in chloroform which corresponds to an optical purity of 63.9%.

EXAMPLE 18

A solution of 143 mg. S(−)proline ethyl ester dissolved in 0.5 ml. acetonitrile was added to a solution of 182 mg. 2-methyl-2-(3-oxobutyl)-1,3-cyclopentanedione dissolved in 0.5 ml. acetonitrile and the resulting reaction mixture was stirred under an atmosphere of argon at a temperature of 20°-23° C. for 20 hours. The reaction mixture, without removal or reagent or solvents, was chromatographed on thin layer plates of silica gel and a fraction of 68 mg. (41.5%) corresponding to a mixture of (+)-7,7a-dihydro-7aβ-methyl-1,5(6H)-indandione and starting trione was isolated as an oil; $[\alpha]_D^{25} +13.6°$, c=0.994% in benzene. Upon examination by uv spectroscopy, $\lambda_{max}^{MeOH}$ 232 mμ (ε6,770), it was determined to be 61% enone and thereby an optical yield of 6.07% was calculated.

EXAMPLE 19

50 Mg. of (+)-3a,4,7,7a-tetrahydro-3aβ-hydroxy-4αα,,7aβ-dimethyl-1,5(6H)-indandione, $[\alpha]_D^{25} +34.60°$, c=1.0% in chloroform; was dehydrated according to the procedure of Example 6 to give an oil, 43.1 mg. (95%) of (+)-7,7a-dihydro-4,7aβ-dimethyl-1,5(6H)-indanedione, $[\alpha]_D^{25} +297.48°$, c=1.07% in chloroform; $\lambda_{max}^{MeOH}$ 248.5mμ (ε 11,980); ir peak maxima in chloroform solution at 1745 and 1660 cm$^{-1}$; nmr in $CDCl_3$: δ1.31 singlet (C-7a,$\underline{CH_3}$), 1.82 singlet (C-4, $\underline{CH_3}$).

EXAMPLE 20

By the general method as given in Example 1, a total of 63 g. of 2-methyl-1,3-cyclohexanedione was reacted with 83 ml. methyl vinyl ketone in 120 ml. demineralized water at 20° C. for seven days to give after work up and fractional distillation, 83.6 g. (85%) of a yellow oil, bp. 110°-115° at 0.025 mm. Hg. which was the pure 2-methyl-2-(3-oxobutyl)-1,3-cyclohexanedione.

EXAMPLE 21

A total of 19.6 g. of 2-methyl-2-(3-oxobutyl)-1,3-cyclohexanedione was dissolved in 100 ml. of anhydrous N,N-dimethylformamide. The resulting solution was cooled to 0° C. and 115 mg. of S(−)proline was added in small portions over a period of 30 minutes. The reaction mixture was permitted to come to 20°-23° C. and a nitrogen atmosphere was maintained over the suspension which was also protected from light. After 24 hours, 115 mg. additional S(−)proline was added to the mixture and a similar addition of S(−)proline was repeated after 48 hours. The reaction was terminated after a total of 72 hours of stirring by high vacuum distillation of the solvent to give a dark residue that was dissolved in 400 ml. diethyl ether, stirred with 5.0 g. of activated charcoal and filtered through 5.0 g. of silica gel to give an orange colored filtrate that upon storage for 16 hours at 0° C. deposited 3.4 g. (17.3%) of crude crystalline (−)-3,4,4a, 5,8,8a-hexahydro-4aβ-hydroxy-8aβ-methyl-1,6-(2H,7H)-naphthalene-dione; $[\alpha]_D^{25}$ −19.83°, c=1.22% in chloroform, m.p. 131.5°-141.5° C. Evaporation in vacuo of the solvent from the mother liquor produced a residual oil that subsequently gave 2 additional crystalline crops: one of 2.4 g. (12.2%); $[\alpha]_D^{25}$ −18.2°, c=1.015% in chloroform; m.p. 129°-133° and another of 1.26 g. (6.4%); $[\alpha]_D^{25}$ −15.39°, c=1.04% in chloroform; m.p. 131°-135°.

Chromatography on silica gel of the remaining oil gave a total of 3.18 g (16.2%) of the aforesaid crude product, average $[\alpha]_D^{25}$ −11.57° in chloroform and 6.95 g. (35.5%) of starting trione. The overall yield of crude reaction product was calculated as 10.24 g. (52.1%) of average $[a]_D^{25}$ −16.33°. An optically pure sample was obtained by recrystallization from ether and had m.p.

134.5°–135.5° C; $[a]_D^{25}$ −21.97°, c=1.1013% in chloroform; ir maxima in chloroform at 3625, 3450 and 1725 cm$^{-1}$; nmr in CDCl$_3$: δ1.31 singlet (C-8a-$\underline{CH_3}$), 2.52 singlet (C-4a-O$\underline{H}$). The above product may be dehydrated using the procedure of Example 6 to yield in crude form (+)-3,4,8,8a-tetrahydro-8a-methyl-1,6-(2H,7H)-naphthalenedione as an oil; $[a]_D^{25}$ +75°, c=1.00% in benzene; $\lambda_{max}^{MeOH}$ 240 mμ(ε9,460). This represents a 75% optical purity and 75.2% purity by uv spectroscopy and thus it is equivalent to 99.8% optical yield.

EXAMPLE 22

A total of 7.84 g. of 2-methyl-2-(3-oxobutyl)-1,3-cyclohexanedione was dissolved in 40 ml of anhydrous N,N-dimethylformamide and 7.84 g. of activated charcoal was added to give a black suspension that was stirred under an argon atmosphere. Then there was added at one time 1.4 g. of S(−)proline and stirring continued at 20°–23° C. for eight days. The mixture was filtered through paper by vacuum and the resulting filter cake was washed thoroughly with ether and finally the filtrate was diluted to a volume of approximately 500 ml. The dark ether solution was washed three times with small amounts of dilute hydrochloric acid to give a nearly colorless ether layer. The combined aqueous portions were extracted two times with a total of 200 ml. of ether and then the combined ether extracts were dried over anhydrous sodium sulfate, filtered and evaporated to a constant weight in vacuo to give 7.09 g. (90.5%) of an oil, which crystallized (identical to conjugated ketone from Example 21) and had; $[a]_D^{25}$ +63.70°, c=1.185% in benzene; $\lambda_{max}^{EtOH}$ 243/4 mμ (ε 10,970); ir maxima in chloroform, 1715, 1665 and 1620 cm$^{-1}$; nmr in CDCl$_3$: δ1.48 singlet (C-8a-$\underline{CH_3}$), 5.88 singlet (C-5 proton). This represents an optical purity of 63.7% and a uv purity of 87.2% and thereby giving an optical yield of 73.2%.

EXAMPLE 23

A total of 177 mg. of (±)-2-methyl-2-(3-oxobutyl)cyclopentanone was dissolved in 1.0 ml. of anhydrous N,N-dimethylformamide and 12.5 mg. of S(−)proline was added at one time. The resulting mixture was stirred at 20°–23° C. under an atmosphere of argon for 24 hours. The reaction mixture was filtered through 1.6 g. of silica gel and the absorbent was rinsed with 50 ml. of ethyl acetate and the filtrate evaporated in vacuo to give an oil of 784 mg. that still contained N,N-dimethylformamide. Purification by preparation thin layer chromatography on silica gel gave a fraction of 25.1 mg. (14% of a maximum theoretical 43%) of an oil, (−)-7aβ-methyl-3aβ-hydroxy-3a,6,7,7a-tetrahydro-5(4H)-indanone $[a]_D^{25}$ −8.53°, c=1.255% in chloroform; ir maxima in chloroform solution at 3650, 3550-3400 and 1710 cm$^{-1}$. Another fraction was obtained of an impure oil that weighed 106.2 mg. (60%) and had $[a]_D^{25}$ +5.08°, c=1.062% in chloroform. The R$_f$ value of this material was identical to that of starting dione. Similar reaction conditions on this latter described material using R(+)proline gave, after preparative thin layer chromatography on silica gel, a product as an oil of 19.9 mg. (11.2% of a maximum theoretical 43%) of (+)-7aα-methyl-3aα-hydroxy-3a,6,7,7a -tetrahydro-5(4H)indanone, [a]25/D +10.55°, c=0.995% in chloroform; ir maxima in chloroform solution at 3625, 3500-3400 and 1708 cm$^{-1}$.

EXAMPLE 24

A total of 660 mg. of (±)-3-tert.butoxy-1,2,3,3a,4,5,8,9,9aβ, 9bα-decahydro-6-(3-oxobutyl)-3aβ-methyl-7H-benz[e]inden-7-one was hydrogenated according to the literature over 5% palladized carbon in 95% aqueous ethanol containing 0.2% triethylamine at atmospheric pressure to give upon removal of the catalyst by filtration and subsequent evaporation of the solvent in vacuo, an oil weighing 665 mg. (100%) that was uniform by thin layer chromatography and had: ir maxima in chloroform solution at 1712, 1365, 1390 amd 1080 cm$^{-1}$; nmr in CDCl$_3$: δ0.80 singlet (C-18-$\underline{CH_3}$), 1.13 singlet (9H of t-butyl), 2.13 singlet

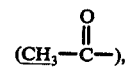

3.41 singlet (C-17-$\underline{H}$). This compound was (±)-3β-tert.butoxy-6(3-oxobutyl)-3aβ-methylperhydro-benz[e]indan-7-one.

EXAMPLE 25

A solution comprised of 348 mg. of the aforesaid hydrogenation product dissolved in 1.0 ml. of anhydrous N,N-dimethylformamide was stirred with 17.5 mg. of S(−)proline at 20°–23° C. under an atmosphere of argon for 24 hours. The mixture was diluted with 10 ml. of ether and the proline along with a precipitated impurity totaling 110.5 mg. was separated and the filtrate was evaporated under high vacuum of approximately 0.1 mm/Hg and 35° C to give 268 (77%) of a dark oil that was separated by preparative thin layer chromatography into two major fractions. The first fraction was a partially crystalline product of 36.2 mg. (10.4%); $[a]_D^{25}$ −4.8°, c=1.00% in chloroform; ir maxima in chloroform solution at 3550, 3500-3350, 1710, 1385 and 1355 cm$^{-1}$; the second fraction was an oil of 73.3 mg. (21%) that was uniform by thin layer chromatography and had $[a]_D^{25}$ −3.0°, c=2.0% in chloroform, but was obviously a mixture of unreacted material and products as shown by uv spectroscopy, $\lambda_{max}^{MeOH}$ 238-9 mμ (ε5,930); ir maxima in chloroform at 3550, 3500-3350, 1710, 1660, 1620, 1380 and 1355 cm$^{-1}$.

Dehydration and hydrolysis of the tert.butyl group of the partially crystalline first fraction (33.5 mg.) was accomplished by refluxing in a 50:50 mixture (5.0 ml.) of 2N hydrochloric acid and methanol for 5 hours under a nitrogen atmosphere. The resulting mixture was cooled in an ice-bath and neutralized with aqueous sodium hydroxide and then all solvents were removed by evaporation at 30° C. and 0.05 mm/Hg to give a dry residue that was broken up in ethyl acetate. Filtration followed by evaporation in vacuo gave a mixture as an oil, 26.3 mg. (100%). Purification by preparative thin layer chromatography on silica gel gave a fraction of 5.2 mg. (19.8%) of an oil, [a]25/D −22.4°, c=0.433% in chloroform; $\lambda_{max}^{EtOH}$ 239 mμ (ε 11,730); ir spectrum was superimposable with both that of authentic 19-nortestosterone and racemic 19-nortestosterone and had ir maxima at 3675, 3550-3350, 1665 and 1620 cm$^{-1}$. Thin layer chromatographic analysis showed it to be uniform and with an identical R$_f$ value as authentic 19-nortestosterone; CD in dioxane solution showed a multiple positive Cotton Effect centered at 333 mμ that was the mirror image of authentic 19-nortestosterone and confirmed the structure as levorotatory 19-nortestosterone.

This represents an optical purity of 38.2% and by calculation based upon uv spectroscopy, a 55.4% optical yield. Another fraction of the chromatography amounted to 4.2 mg. (16%) of a crystalline product, $[a]_D^{25}$ −17.7°, c=0.35% in chloroform; $\lambda_{max}^{EtOH}$ 241 mμ (ε 13,950); ir maxima in chloroform at 3650, 3350–3350, 1660 and 1620 cm$^{-1}$; CD in dioxane solution showed a multiple positive Cotton Effect; thin layer chromatographic analysis showed it to be uniform and the same $R_f$ as authentic retro-(9β,10α) 19-nortestosterone. This represents an optical purity of 16.9% and by calculation based upon uv spectroscopy, a 20.9% optical yield.

EXAMPLE 26

In the identical manner as in Example 25, the hydrogenation product of Example 24 was cyclized in the presence of R(+)proline and dehydrated to afford (+)-19-nortestosterone and the (+)antipode of 19-nor-retrotestosterone.

EXAMPLE 27

A total of 34.5 mg. of S(−)proline was added at one time to a solution of 316 mg. of 2-methyl-2-(6-m-methoxyphenyl)-3-oxohexyl)-1,3-cyclopentanedione dissolved in 1.0 ml. of anhydrous N,N-dimethylformamide and the resulting suspension was stirred at 60° C. under a nitrogen atmosphere for 38 hours. The mixture was filtered to eliminate unreacted proline and the filtrate was evaporated to a dark residual oil at 25° C. and 0.05 mm Hg. Separation of the product from unreacted starting trione was accomplished by thin layer chromatography on silica gel to yield 51.2 mg. (16.2%) of (+)-3a,4,7,7a-tetrahydro-3aα-hydroxy-4β-(3′-methoxyphenethyl)-7aα-methyl-1,5(6H)-indanedione as an oil; $[a]_D^{25}$ +30.0°, c=2.0% in chloroform; ir maxima in chloroform solution at 3650, 3550–3400, 1740, 1720, 1605, 1585 and 1255 cm$^{-1}$.

EXAMPLE 28

Ring closure and dehydration according to the general procedure of Example 6 gave the optical antipode of the known (−)-3-methoxyestra-1,3,5(10),8,14-pentaen-17-one as an oil in 76% yield. This compound was characterized by ir: maxima in chloroform solution at 1740, 1655, 1600, 1550, and 1250 cm$^{-1}$; and and uv spectroscopy, $\lambda_{max}^{MeOH}$ 312 mμ (ε 45,00), 228 mμ(ε 26,700); and had $[α]_D^{25}$ +45.3°, c=2.00% in chloroform which calculates to an optical purity of 45.3%.

EXAMPLE 29

In an indentical manner to Example 27 2-methyl-2-(6-m-methoxyphenyl-3-oxohexyl)-1,3-cyclopentanedione was cyclized in the presence of R(+)proline to afford (−)-3a,4,7,7a-tetrahydro-3aβ-hydroxy-4α-(3′-methoxyphenethyl)-7aβ-methyl-1,5(6H)-indanedione.

EXAMPLE 30

The product of Example 29 was ring closed and dehydrated according to the procedure of Example 6 to afford known (−)-3-methoxyestra-1,3,5(10),8,14-pentaen-17-one.

We claim:
1. Compounds of the formula

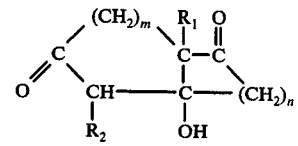

where $R_1$ is lower alkyl, lower alkenyl, lower alkynyl or halogen; $R_2$ is phenyl, phenyl substituted with halogen, lower alkyl, lower alkoxy and nitro, benzyl, metamethoxybenzyl, phenethyl or meta-methoxyphenethyl; $n$ is an integer between 1 and 5 inclusive and $m$ is an integer between 1 and 4 inclusive.

2. The compound of claim 1 which is (+)-3a,4,7,7a-tetrahydro-3aα-hydroxy-4β-(3′-methoxyphenethyl)-7aα-methyl-1,5(6H)-indanedione.

3. The compound of claim 1 which is (−)-3a,4,7,7a-tetrahydro-3aβ-hydroxy-4α-(3′-methoxyphenethyl)-7aβ-methyl-1,5(6H)-indanedione.

* * * * *